United States Patent [19]

Ezcurra

[11] Patent Number: 5,328,361
[45] Date of Patent: Jul. 12, 1994

[54] ORTHODONTIC PLIER-TYPE LIGATURE CUTTERS

[75] Inventor: Al Ezcurra, South Pasadena, Calif.

[73] Assignee: Ormco Corporation, Glendora, Calif.

[21] Appl. No.: 60,206

[22] Filed: May 7, 1993

[51] Int. Cl.$^5$ ............................ A61C 3/00; A61C 3/14; A61C 3/16
[52] U.S. Cl. .......................................... 433/4; 433/159
[58] Field of Search .................... 433/3, 4, 153, 157, 433/159

[56] References Cited

U.S. PATENT DOCUMENTS

| | | |
|---|---|---|
| 3,209,458 | 10/1965 | Rosen . |
| 3,638,316 | 2/1972 | Cusato . |
| 3,727,316 | 4/1973 | Goldberg . |
| 3,781,993 | 1/1974 | Cusato ................................. 433/4 |
| 3,804,132 | 4/1974 | Mann . |
| 4,035,917 | 7/1977 | Roberts . |
| 4,040,186 | 8/1977 | Kalvelage ............................ 433/4 |
| 4,395,824 | 8/1983 | Puro . |
| 4,669,979 | 6/1987 | Snead . |
| 5,257,558 | 11/1993 | Farzin-Nia et al. .................. 81/418 |

OTHER PUBLICATIONS

A. G. Russell's Hunter's Scalpel, Knife advertisement "American Rifleman" p. 31.
A. G. Russell's Hunter's Scalpel, Knife advertisement A. G. Russell, Winter Catalogue, 1992, p. 22.
ATS34 High Quality Knife Material, Hitachi.
Ormco Corporation Catalogue, "New line of brazed cutters from AEZ".

Primary Examiner—Gene Mancene
Assistant Examiner—Cindy A. Cherichetti
Attorney, Agent, or Firm—Wood, Herron & Evans

[57] ABSTRACT

An orthodontic cutter for cutting portions of orthodontic metal ligatures and the like having a pair of ATS-34 stainless steel plier halves, uniformly heat treated to within the range of about RC 57-59, with each plier half being of one piece construction and free of abrupt changes in width along its length, with the width being measured perpendicular to both the longitudinal axis of the plier half and the pivot axis. The entire orthodontic cutter is corrosion resistant and holds its edge without fracturing.

3 Claims, 1 Drawing Sheet

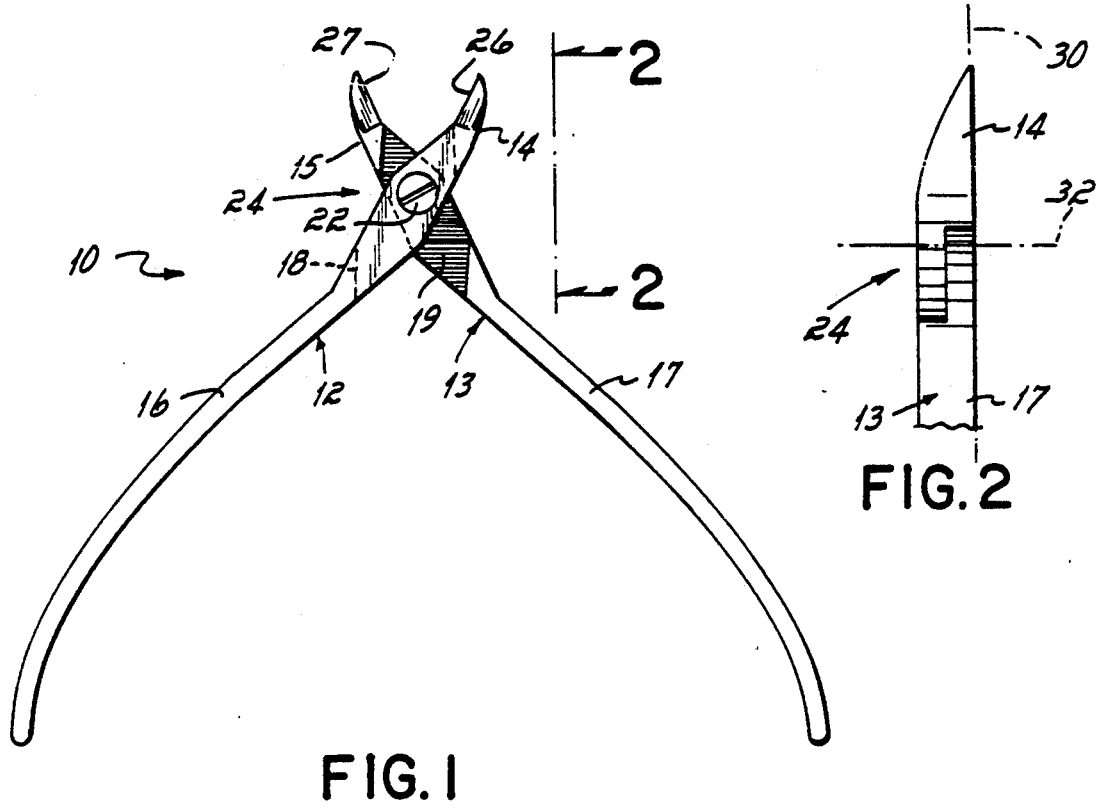

ORTHODONTIC PLIER-TYPE LIGATURE CUTTERS

FIELD OF THE INVENTION

This invention relates to plier-type cutters used to cut orthodontic ligatures and the like.

BACKGROUND OF THE INVENTION

Plier-type cutters are often used in orthodontics to cut stainless steel, titanium alloy or other orthodontic metal ligatures and similar appliances. These orthodontic cutters typically include a pair of plier halves, with each plier half having a handle, a pivot section, and a cutting jaw. The two plier halves are pivotally connected at their pivot sections such that relative movement of the handles will cause relative movement of the jaws. Heretofore, one form of these cutters employed cutting edge inserts made of carbide or tool steel which were blazed or otherwise secured to the cutting jaws, with the balance of the cutting jaws and the associated handle being made of stainless steel, typically 17-4. Such cutting edge inserts were used because known stainless steel compositions were not as suitable for use as cutting edges of orthodontic cutters. The cutting edges of prior cutters, which did not use inserts, were made with stainless steel plier halves of one piece construction and were prone to fracture in use or loss of their edge in a relatively short time. On the other hand, cutters with cutting edges formed on carbide or tool steel inserts typically maintained their edge without fracturing.

In the orthodontic field, as in other medical fields, it is important to maintain clean and sterile instruments. Orthodontic cutters are typically cleaned or sterilized with high temperature steam after every use. The cleaning and sterilizing procedures, and even the orthodontic procedures in which they are used, often subject the cutters to corrosive environments. While carbide and tool steel cutting edge inserts enable the cutter to hold its cutting edge without fracturing, they are not as corrosion resistant as the remaining stainless steel portion of the cutter. Thus, the known carbide and tool steel inserts had a tendency to corrode after only limited use, requiring costly re-work or replacement. Another disadvantage with known orthodontic cutters using cutting edge inserts is the relatively high cost of manufacturing the inserts and the mounting thereof to the cutter jaws.

SUMMARY OF THE INVENTION

An objective of the present invention is to provide a single piece orthodontic cutter for cutting orthodontic metal ligatures which is less likely to corrode to the point of requiring re-work or replacement as a result of use and frequent cleaning or sterilization.

Another objective of the present invention is to provide a single piece corrosion-resistant orthodontic ligature cutter which exhibits satisfactory cutting edge life.

An additional objective of the present invention is to provide a single piece corrosion-resistant orthodontic ligature cutter which exhibits an increased resistance to fracturing.

A further objective of the present invention is to provide a single piece corrosion-resistant orthodontic cutter which can be manufactured at a relatively low cost.

These objectives are accomplished by providing a plier-type orthodontic cutter for cutting of orthodontic metal ligatures having two moveable plier halves in which each plier half is of one piece construction and made of ATS-34 stainless steel made by Hitachi. Each of the plier halves is heat treated to have a generally uniform hardness in the approximate range of about RC 57-59. Each of the plier halves has a cutting jaw section at one end with a cutting edge, a handle section at the other end, and a pivot section therebetween. The plier halves are connected together in a pivotal relationship at their pivot sections such that relative movement of the handle sections causes relative movement of the jaw sections and contact of the cutting edges. Each of the plier halves is free of abrupt changes in width along the length thereof, with each plier half exhibiting only gradual changes in width, with the width being measured perpendicular to both the length and pivot axis. In addition, the handle and cutting jaw section of each plier half exhibits an increase in cross sectional area, mainly increase in width, where they join the pivot section. Due to the use of ATS-34, heat treatment to the hardness noted, and plier halves with the above configuration, the ligature cutters not only exhibit a high degree of corrosion resistance when subjected to orthodontic use with repeated high temperature steam sterilization, but they also hold their cutting edge without fracturing after repeated use over long periods.

By reason of the foregoing plier construction features, including the specific ATS-34 stainless steel used, heat treatment provided and gradually changing width configuration, an orthodontic ligature cutter is provided which adequately holds its edge without fracturing when cutting various orthodontic metal ligature-like appliances and yet withstands corrosion even when subjected to repeated sterilization procedures with high temperature steam. Further, the cost of manufacturing the orthodontic cutter of this invention is significantly reduced by virtue of the elimination of any cutting edge insert.

The above and other objections and advantages of the present invention will become more apparent from the following detailed description of the invention.

BRIEF DESCRIPTION OF THE DRAWINGS

FIG. 1 is a top plan view of a preferred embodiment of the orthodontic cutter according to the present invention; and FIG. 2 is a side elevational view taken along lines 2—2 of FIG. 1;

DETAILED DESCRIPTION OF THE INVENTION

FIGS. 1 and 2 illustrate an orthodontic plier-type ligature cutter 10 of this invention which can be used to cut orthodontic stainless steel ligatures and the like (not shown). The cutter 10 has two single piece plier halves 12, 13, having respective cutting jaw sections 14, 15 at one end thereof, handle sections 16, 17, respectively, at the other end, and recessed pivot sections 18, 19 therebetween, respectively. The recessed pivot sections 18, 19 are adapted to receive each other in nesting relation and are pivotally connected together, for example, by a screw 22 to form a pivot joint 24. An integral compression cutting edge 26, 27 is formed along the cutting jaw section 14, 15 of each plier half 12, 13, respectively. When the recessed pivot sections 18, 19 are connected together by the joint screw 22, the pivot joint 24 allows pivotal movement between the plier halves 12, 13 such that relative movement of the handle sections 16, 17 causes the jaw sections 14, 15 to open or close and thus the cutting edges 26, 27 to separate or make contact in cutting relation.

The width of each plier half 12, 13 of the present cutter 10 changes gradually in both directions from its pivot section 18, 19, that is, the width changes gradually from the pivot section to its handle section 16, 17 and to its cutting jaw section 14, 15. This is done to help minimize the likelihood of fracturing. In a preferred form, the width of the pivot sections 16, 17 changes from a maximum in the approximate center thereof to approximately fifty percent (50%) of the maximum where the ends of the pivot sections join their respectively associated handle and jaw sections. For the purposes of this description, the width of each of the plier halves of cutter 10 is measured perpendicular to both its longitudinal axis, designated 30, and its pivot axis, designated 32, and the thickness of each is measured parallel to pivot axis 32. Stated differently, the pivot sections 18, 19 have a generally rhomboidal shape when viewed in top plan view with the major axis approximately twice the length of the minor axis. In order to further minimize the likelihood of fracturing, the bottom of each recessed section 18, 19 is formed with rounded edges, preferably having a typical radius of about 0.030±0.005".

Each plier half 12, 13 is of one piece construction and made from the same stainless steel, preferably ATS-34 manufactured by Hitachi Metals America, Ltd., Materials Trading Division, 5000 East Spring Street, Suite 360, Long Beach, Calif., 90815. This stainless steel generally comprises by weight:
carbon: about 1.05%
silicon: about 0.02%
manganese: about 0.04%
chromium: about 14.00%
molybdenum: about 4.00%
iron: balance.

Ligature cutters 10 having one piece plier halves 12, 13 made of the Hitachi ATS-34 stainless steel have been found to be sufficiently corrosion resistant for orthodontic applications. In addition, unlike any other stainless steel known, plier halves 12, 13 made of this steel can be uniformly heat treated to an overall hardness for maintaining or holding its cutting edges 26, 27 with little, if any, likelihood of a fracture occurring.

Holding the cutter 10 in one hand, an orthodontist can cut the desired ligatures or similar orthodontic metal appliance (not shown) by spreading the handle sections 16, 17 apart, therein opening the cutting jaw sections 14, 15, positioning the ligature between the two cutting edges 26, 27, and squeezing the handle sections 16, 17 together, thereby closing the jaw section 14, 15, until the ligature is severed by the cutting edges 26, 27.

After being formed, each of the plier halves 12, 13 is heat treated so as to retain their corrosion resistance and so that the cutting edges 26, 27 are hard enough to adequately hold their edge. It has been found that a satisfactory compromise between hardness and resistance to fracture is reached when the plier halves 12, 13 of ligature cutter 10 are heat treated to within a hardness range of about RC 57-59. The heat treating process used begins with a preheating step of heating each plier half 12, 13, at a uniform ramp rate for about one-half hour, to a temperature within the range of about 600°-700° C., and holding them within that temperature range for about one hour. The plier halves 12, 13 are then austenitized by heating them, at a uniform ramp rate for about one-half hour, to a temperature within the range of about 1010°-1030° C. and holding them within that temperature range for about one hour. The plier halves 12, 13 are then air quenched or cooled, at a uniform ramp rate for about one-half hour, to room temperature. After this initial quenching step, the plier halves 12, 13 are subjected to two tempering steps. In the first temper, the plier halves 12, 13 are heated, at a uniform ramp rate for about one-half hour, to a temperature of about 225° C., held at that temperature for about one and a half hours, and then air cooled, at a uniform ramp rate for about one-half hour, to room temperature. In order to complete the martensitic transformation of the steel, after the plier halves 12, 13 have reached room temperature, they are quenched to about −100° C. by being transferred to a nitrogen-filled cryogenic box and held at that temperature for about two hours. It takes about 15 minutes for the plier halves 12, 13 to reach −100° C. after being transferred. Next, the plier halves 12, 13 are removed from the cryogenic box and allowed to warm to room temperature. The plier halves 12, 13 are then subjected to a second and final temper in which they are heated, at a uniform ramp rate for about one-half hour, to a temperature of about 225° C., held at that temperature for about two hours and then air cooled, at a uniform ramp rate for about one-half hour, to room temperature. The above preheat and austenitizing steps are conducted in a vacuum, and the two tempering steps are conducted in air, except for the cryogenic treatment step. The resulting hardness can be increased or decreased by lowering or raising the tempering temperature, respectively.

After heat treatment, the plier halves 12, 13 must be pickled, ground or polished to remove scale. Next, they should be baked in air to within the range of about 121°-149° C. to remove "acid brittleness." Finally, the plier halves 12, 13 should be passivated for about 30 minutes in a solution of 50% by volume nitric acid, balance water, at about 49°-60° C. This passivation treatment should be preceded and followed by about 30 minutes exposure to 5% by weight sodium hydroxide, balance water, at about 71°-82° C. The plier halves 12, 13 should be thoroughly rinsed with distilled water after each of these chemical treatments.

The cutter 10 is intended to be re-used numerous times and subjected to standard orthodontic sterilization procedures subsequent to its use. Therefore, to function properly in this environment, the cutter 10 should not only hold its cutting edge without fracturing, it should also resist the corrosive effects of such repeated and extended use and subsequent sterilization. Unlike prior art orthodontic ligature cutters (not shown) which used corrodible cutting edge inserts in its cutting jaws, the plier halves 12, 13 of the present cutter 10 are made entirely of stainless steel and are fully corrosion resistant. At the same time, because each of the plier halves 12, 13 has the above described configuration and is made of ATS-34 having a hardness within the range of about RC 57-59, the present cutter 10 can hold its edge to a satisfactory degree without fracturing.

In addition, the cutter 10 according to this invention can be manufactured less expensively than prior orthodontic cutters. This reduction in manufacturing costs is attributable to each plier half being of one piece construction, i.e., the elimination of the cutting edge inserts.

While only one embodiment of this invention has been described in detail, this invention is not to be limited solely to this embodiment. A person skilled in the art will readily appreciate changes and modifications which may be made without department from the spirit of the present invention. Therefore, this invention is not intended to be limited except by the scope of the following claims.

What is claimed is:

1. An orthodontic plier-type cutter for cutting portions of orthodontic metal appliances comprising:

a pair of plier halves made of ATS-34 stainless steel having a hardness of at least about RC 57, each of said plier halves being of one piece construction, having an elongated handle section at one end, a cutting jaw section at the other end, and a pivot section located therebetween with a pivot axis passing therethrough, each of said plier halves having a width measured perpendicular to its length and to said pivot axis which increases gradually from its handle section to its pivot section and from its cutting jaw section to its pivot section; and connecting means for connecting the pivot sections of said pair of plier halves together for pivotal motion about said pivot axis such that relative movement of said handle sections toward each other causes relative movement of said cutting jaw sections toward each other.

2. The cutter of claim 1 wherein each of said plier halves has a hardness within a hardness range of about RC 57-59.

3. The cutter of claim 1 wherein each of said pivot sections is generally rhomboidal in shape when viewed in a direction parallel to said pivot axis, with the length of the major axis thereof being at least approximately twice the length of the minor axis thereof.

* * * * *